United States Patent [19]

Aya et al.

[11] 4,039,313
[45] Aug. 2, 1977

[54] HERBICIDAL METHODS USING 4-CHLOROBENZYL-N,N-HEXAMETHYLENETHIOLCARBAMATE

[75] Inventors: Masahiro Aya; Masao Miyamoto; Nobuo Fukazawa, all of Tokyo, Japan

[73] Assignee: Bayer Aktiengesellschaft, Leverkusen, Germany

[21] Appl. No.: 482,174

[22] Filed: June 24, 1974

Related U.S. Application Data

[62] Division of Ser. No. 296,745, Oct. 11, 1972, abandoned.

[30] Foreign Application Priority Data

Oct. 18, 1971 Japan .................................. 46-81698

[51] Int. Cl.$^2$ ............................................. A01N 9/22
[52] U.S. Cl. ....................................................... 71/88
[58] Field of Search ............................................ 71/88

[56] References Cited

U.S. PATENT DOCUMENTS

| 3,224,861 | 12/1965 | D'Amico | 71/88 |
| 3,303,014 | 2/1967 | D'Amico | 71/88 |

OTHER PUBLICATIONS

Aya et al., Chem. Abst., vol. 77, (1972), 1859p – German Pat. 2,138,017.

*Primary Examiner*—Lewis Gotts
*Assistant Examiner*—Catherine L. Mills
*Attorney, Agent, or Firm*—Burgess, Dinklage & Sprung

[57] ABSTRACT 4-chlorobenzyl-N,N-hexamethylenethiolcarbamate has been found to be uniquely active and selective in the control of weeds, particularly in crop cultivations such as rice paddies.

5 Claims, No Drawings

HERBICIDAL METHODS USING 4-CHLOROBENZYL-N,N-HEXAMETHYLENETHIOLCARBAMATE

This is a division, of application Ser. No. 296,745, filed Oct. 11, 1972, now abandoned.

The present invention relates to a certain thiolcarbamic acid ester and its use as a herbicide.

For the controlling of barnyard grass, a weed found in paddy fields, pentachlorophenol (PCP) has been used hitherto. However, this compound is extremely irritative to the mucous membranes of humans, is difficult to regulate, and is also remarkably poisonous to fish. Therefore, its disadvantage is that the application period and the scope for its use are limited.

For the controlling of spikerushes and broad-leafed weeds growing in the same season as barnyard grass, 2-methyl-4-chlorophenoxyacetic acid (MCP) is used. However, MCP is not very effective for controlling barnyard grass.

Accordingly, a mixture of PCP and MCP is generally used for the simultaneous control of barnyard grass, spikerushes and broad-leaved weeds in paddy fields.

It has been disclosed in U.S. Pat. No. 3,224,861 that a herbicidal activity is exhibited by thiol- and dithio-carbamic acid esters of the general formula

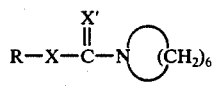

in which

X and X' are each oxygen or sulphur, with the proviso that one of them must be sulphur, and R is a benzyl radical that may optionally be substituted with 1 to 4 halogen atoms.

4-chlorobenzyl-N,N-hexamethylenethiolcarbamate was not specifically disclosed in the aforesaid U.S. Patent, but has now been found to possess outstanding herbicidal properties. Accordingly, the present invention provides a method of combating weeds, which comprises applying to the weeds or a weed habitat the compound of the formula

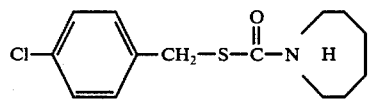

(I)

alone or in admixture with a diluent or carrier.

The present invention also provides methods of growing crops protected from damage by weeds by being grown in areas in which immediately prior to and/or during the time of the growing the compound of the formula (I) was applied, alone or in admixture with a carrier or diluent.

The compound of the formula (I) may be prepared by a process in which a. 4-chlorobenzylmercaptan of the formula

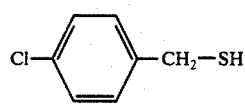

(II)

is reacted, in the form of an alkali metal salt or in the presence of an acid-binding agent, with N,N-hexamethylenecarbamoyl chloride of the formula

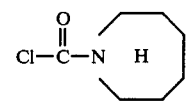

(III)

or (b) a 4-chlorobenzyl halide of the general formula

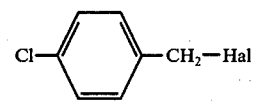

(IV)

in which

Hal is halogen, carbonyl sulphide, COS, and N,N-hexamethylene imine of the formula

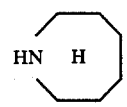

(V)

are reacted together, in the presence of an alkali metal hydroxide or of 'ammonium hydroxide'.

The reaction in process variant (a) is preferably effected in the presence of an inert organic solvent, especially an aliphatic or aromatic hydrocarbon (which may be halogenated), such as benzine, methylene chloride, chloroform, carbon tetrachloride, benzene, chlorobenzene, toluene or a xylene; an ether, such as diethyl ether, dibutyl ether, dioxane or tetrahydrofuran; a low-boiling-point alcohol, such as methanol, ethanol or isopropanol; a ketone, such as acetone; methyl ethyl ketone; methyl isopropyl ketone and methyl isobutyl ketone; or a lower aliphatic nitrile, such as acetonitrile or propionitrile.

As the acid-binding agent, there may be used an alkali metal carbonate or bicarbonate, such as sodium bicarbonate, potassium carbonate or sodium carbonate; an alkali metal alcoholate, such as potassium or sodium methylate or ethylate; or an aliphatic, aromatic or heterocyclic tertiary base, such as triethylamine, diethylaniline or pyridine.

The reaction in process variant (a) may be illustrated by the following equation:

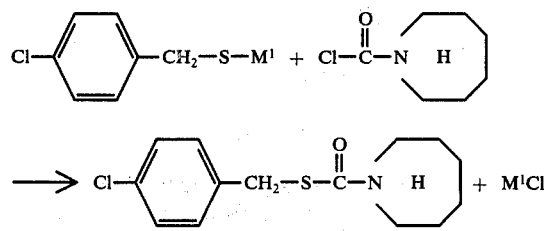

in which $M^1$ is a hydrogen or alkali metal atom.

The reaction of process variant (b) may be effected in the presence of an inert organic solvent, such as one of those mentioned above as being suitable in process variant (a), especially an alcohol or ketone. Water is also a preferred solvent in process variant (b).

The reaction of process variant (b) may be illustrated by the following equation:

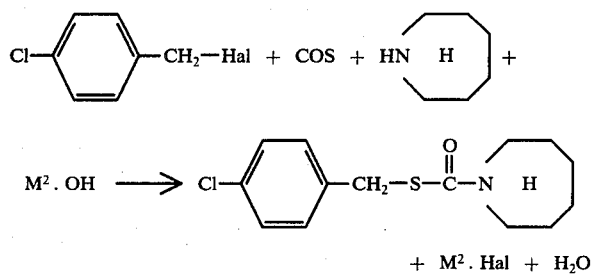

in which
Hal is halogen and
$M^2$ is an alkali metal atom (for example sodium or potassium) or an ammonium radical.

The preparation of the compound of the formula (I) is illustrated in the following Examples.

EXAMPLE 1

Preparation of 4-chlorobenzyl-N,N-hexamethylenethiolcarbamate

To a solution obtained by dissolving 7.9 g (0.05 mole) of 4-chlorobenzylmercaptan in 150 ml of acetone, there were gradually added dropwise 4 g of a 40% aqueous caustic soda solution in order to prepare the sodium salt of 4-chlorobenzylmercaptan. Thereafter, 8.1 g (0.05 mole) of N,N-hexamethylenecarbamoylchloride were gradually added dropwise thereto, while the mixture was being stirred at room temperature. After the addition was over, the reaction was completed by refluxing for 3 – 4 hours. The acetone was distilled off and cold water was added to obtain crude crystals. By recrystallizing the crude product from ethyl alcohol, 11.4 g of white crystals of 4-chlorobenzyl-N,N-hexamethylenethiolcarbamate were obtained. Yield: 80.2% m.p.: 59° – 60° C.

EXAMPLE 2

(Alternate Synthesis)

30 ml of water were added to 15 g (0.15 mole) of N,N-hexamethyleneimine in a 200 ml three-necked flask, and then 20 g (0.125 mole) of a 25% aqueous caustic soda solution were added thereto. The solution was cooled to 0° – 5° C and was stirred continuously.

Then, in separate gas generator, 30 ml of a saturated solution of ammonium thiocyanate were added to a sulphuric acid solution consisting of 145 ml of sulphuric acid and 200 ml of water and the solution was stirred continuously at 20° C slowly to form carbonyl sulphide. The carbonyl sulphide so formed was introduced into the first-mentioned apparatus while the mixture was still being stirred.

After 1 to 2 hours, during which time the temperature in the gas generator had slowly risen from 20° to 50° C, the generation of the carbonyl sulphide was almost complete, so that about 10 g (0.17 mole) of carbonyl sulphide had been introduced into the flask.

After completion of the introduction of the carbonyl sulphide, 16 g (0.1 mole) of 4-chlorobenzylchloride were added in one batch to the flask and the resulting mixture was stirred at 0° – 5° C for 1 hour, followed by further stirring at 20° to 40° C for 4 hours.

The product separated out in the form of white crystals. After filtration, 25 g of the desired product was obtained. Yield: 90% m.p. : 59° – 60° C.

As mentioned above, 4-chlorobenzyl-N,N-hexamethylenethiolcarbamate, the active compound of the present invention, was not specifically disclosed in the above-mentioned U.S. Pat. No. 3,224,861. However, compared with the other active compounds disclosed in the said U.S. Patent or with the known compound benzyl-N,N-hexamethylenethiolcarbamate disclosed in U.S. Pat. No. 3,303,014 and which is of a similar structure, it surprisingly shows not only an excellent herbicidal activity against various paddy-field weeds such as barnyard grass, spikerushes and broad-leaved weeds, but also shows only a low phytotoxicity against rice plants; it also has an extended application period. Therefore, the present invention has a high practical utility.

Heretofore, in order to control paddy-field weeds, especially barnyard grass, it has generally been necessary to apply herbicides to the paddy fields four to eight days after the transplantation of the rice plants, that is before the germination of the barnyard grass or during the 0 to 1.5-leaved stage thereof, because in general, barnyard grass, as it grows, increases its resistance against herbicides. Furthermore, it was observed that when paddy fields were treated with known herbicides before transplantation of the rice plants or before germination of the barnyard grass, the rice plants to be grown in the paddy fields were subjected to phytotoxicity. Thus prior-art herbicidal compositions were effective in controlling barnyard grass only when they were applied after rice transplantation and during the initial stage of growth of the barnyard grass. Therefore, weed-control treatment was necessary many times to control weeds occurring at a later time. In the circumstances, there has been a great demand for a herbicide that has an extended period of application, with a view to saving labour in cultivation.

The compound of the formula (I) shows excellent and selective herbicidal activities not only against aquatic weeds, particularly barnyard grass, belonging to the Gramineae family and perennial weeds such as spikerushes, but also against, in particular, broad-leaved weeds, against which prior herbicides are less effective. Furthermore, the present compound shows no phytotoxicity against rice plants; therefore it is an unexpectedly good herbicide having a very extended period of use, beginning from the time before germination of the barnyard grass (before transplantation of the rice plants) and continuing to the 2-to 3-leaved stage of the weed (10 to 15 days after the transplantation of the rice plants).

The compound of the present invention is characterized by strong herbicidal activities not only when used before germination of barnyard grass but also when used at the 2-to 3-leaved stage of the weed, under irrigation conditions in either case. Moreover, as it shows no appreciable phytotoxicity against rice plants, it may be effectively and safely used at any time during its extensive application period.

The foregoing is particularly advantageous in view of the fact that most of the commercially available herbicides are efficacious for barnyard grass only at the pre-emergence stage or immediately after emergence of the plants. Further, other substituted benzylthiolcarbamic acid esters, as mentioned above, do not generally show an adequate controlling effect against broad-leaved weeds. Surprisingly, however, the compound of the present invention is characterized by an excellent herbicidal activity against such weeds. Moreover, because of its low phytotoxicity against rice plants, the compound used in the present invention can control such aquatic weeds and yet save much labor in cultivation, when applied before the transplantation of rice plants up to a week or two after the transplantation, a period for which no proper controlling method is in general use at present.

The active compound according to the present invention can be converted into the usual formulations, such as solutions, emulsions, suspensions, powders, pastes and granulates. These may be produced in known manner, for example by mixing the active compound with extenders, that is, liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquified gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates; and preferred examples of dispersing agents include lignin, sulphite waste liquors and methyl cellulose.

The formulations contain, in general, from 0.1 to 95% preferably from 0.5 to 90%, by weight of the active compound.

The compound of the present invention can, if desired, be applied with other agricultural chemicals such as insecticides, acaricides, nematocides, fungicides, antiviral agents, herbicides and plant-growth regulators, as well as with fertilizers. Various adjuvants that are known in the art may also be employed.

The ready-to-use preparations (which may be prepared from suitable formulations by, for instance, dilution with water) may be applied in any usual manner, for instance, by spraying, such as liquid spraying, misting, atomizing, dusting, scattering, watering, fumigating, by soil application, such as mixing, sprinkling, vaporising and irrigating, by surface application, such as painting, banding and dressing (dust-coating), or by immersion.

The amount of active compound in the ready-to-use preparation is generally from 0.001 – 10% by weight, preferably 0.005 – 5% by weight. The quantity of the active ingredient can be varied according to the type of preparation used, the method, purpose, time and place of the application and the growth state of the weeds to be controlled.

The compound according to the present invention may be also used in accordance with the well-known ultra-low-volume (ULV) process. According to this method, it is possible to use a concentration of active ingredient of up to 95%, or even to apply the active compound alone.

The dosage per unit area is generally 0.5 to 20 kg, preferably 1 to 10 kg, by weight of active compound per hectare. However, it is possible to increase or reduce the usual amount and, in special cases, it may actually be necessary to do so.

Compositions containing the active compound of the formula (I) are illustrated in the following Examples, which do not in any way limit the invention. Parts and percentages are by weight.

Example (i)

5 parts of the compound of this invention and 95 parts of a mixture of talc and clay were ground and mixed to form a powder for application by dusting.

Example (ii)

20 parts of the compound of this invention, 75 parts of kaolinite, 3 parts of the sodium salt of an alkylbenzenesulphonic acid and 2 parts of sodium dinaphthylmethanedisulphonate were ground together and then formulated into a wettable powder suitable for application.

Example (iii)

20 parts of the compound of this invention, 75 parts of xylene and 5 parts of polyoxyethylene alkyl aryl ether were mixed together and stirred to form an emulsifiable concentrate, which was diluted with water before application.

Example (iv)

The compound of this invention was dissolved in xylene by heating, and the solution was sprayed onto granular clay. The resulting granules containing about 10% of the active ingredient were directly scattered onto a soil surface.

The herbicidal activity of the compound of the formula (I) is illustrated in and by the following test Examples.

Example A

Test Against Paddy-field Weeds Under Irrigation Conditions (Soil-incorporation Treatment)

Preparation of the Active-compound Formulation:

Carrier (Solvent): 5 parts by weight of acetone
Emulsifier: 1 part by weight of benzyloxypolyglycol ether 1 part by weight of the active compound and the abovementioned amounts of the emulsifier and carrier were mixed to form an emulsifiable concentrate. The mixture was diluted with water to the desired concentration.

Test Procedure

Pots made of a synthetic resin and each having a diameter of 28cm were filled with screened soil from a paddy field. The soil in the pots was irrigated to a depth of 2 cm. The active compound was administered dropwise in the form of an emulsion, as described above, in a fixed quantity by means of a pipette and thereafter was incorporated into the soil to a depth of 15 cm from the soil surface, so that the active compound might be uniformly distributed through the soil layer.

Into the so-treated soil in each of the pots, further soil containing, in quantity, seeds of barnyard grass and seeds of other common paddy-field weeds was incorporated to a depth of 2 cm from the soil surface. Then two rice-plant seedlings (Kinmaze variety) at the two-leaved stage were planted at the center of the soil surface. Finally, cut pieces of spikerush (2 × 2 cm) were planted in the soil surface. Thereafter, the soil was kept under irrigation conditions to a depth of about 3 cm. After 4 weeks, the herbicidal effect on the weeds and the phytotoxicity to the rice plants were evaluated and classified on a scale from 0 to 5 as follows:

Herbicidal Effect as Evaluated in Comparison With Untreated Control

5: more than 95% destruction (perished)
4: more than 80% up to 95% destruction
3: more than 50% up to 80% destruction
2: more than 30% up to 50% destruction
1: more than 10% up to 30% destruction
0: 10% destruction or less (no effect)

Phytotoxicity Against Rice Plants as Evaluated in Comparison With Untreated Control 5: more than 90% damage (fatal)
4: more than 50% up to 90% damage
3: more than 30% up to 50% damage
2: from 10% to 30% damage
1: less than 10% damage
0: no damage (no phytotoxicity)

The results are shown below in Table 1.

Table A.

Test against paddy-field weeds under irrigation conditions (soil-incorparation treatment)

| Compound | Amount of active ingredient (g/10 are) | Herbicidal Effect | | | | Phytotoxicity to Rice plants |
|---|---|---|---|---|---|---|
| | | Barnyard grass | Umbrella-sedge | Spikerushes | Broad-leaved weeds | |
| 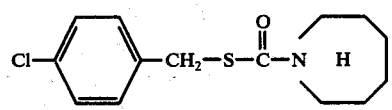 (I) | 400<br>200<br>100 | 5<br>5<br>4 | 5<br>5<br>5 | 5<br>4<br>3 | 5<br>5<br>4 | 0<br>0<br>0 |
| 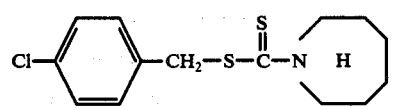 (Comparison No.1) | 2000<br>1500<br>1000 | 3<br>1<br>0 | 4<br>3<br>0 | 3<br>2<br>0 | 0<br>0<br>0 | 1<br>0<br>0 |
| 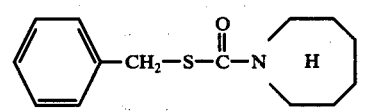 (Comparison No.2) | 1500<br>1000<br>500 | 4<br>3–4<br>3 | 5<br>4<br>3 | 3<br>2<br>0 | 3<br>1<br>0 | 5<br>5<br>4 |
| 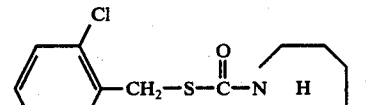 (Comparison No.3) | 1500<br>1000<br>500 | 4<br>3<br>0 | 4<br>3<br>1 | 3<br>2<br>0 | 4<br>3<br>1 | 4<br>3<br>2 |
| 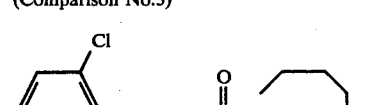 (Comparison No.4) | 1500<br>1000<br>500 | 5<br>3–4<br>3 | 5<br>4<br>3 | 3<br>2<br>1 | 3<br>3<br>1 | 5<br>4<br>3 |
| 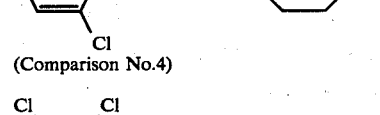 (Comparison No.5) | 1500<br>1000<br>500 | 4<br>3–4<br>3 | 4<br>3<br>0 | 3<br>0<br>0 | 4<br>2<br>1 | 5<br>2–3<br>2 |

Table A.-continued

Test against paddy-field weeds under irrigation conditions
(soil-incorparation treatment)

| Compound | Amount of active ingredient (g/10 are) | Herbicidal Effect | | | | Phytotoxicity to Rice plants |
|---|---|---|---|---|---|---|
| | | Barnyard grass | Umbrella-sedge | Spikerushes | Broad-leaved weeds | |
| Non Treatment | | 0 | 0 | 0 | 0 | 0 |

Notes:
1. Broad-leaved weeds: *Monochoria, Rotala indica* and *Lindernia pyxidaria*
2. The comparison compounds Nos. 1, 3, 5 are disclosed in U.S. Pat. No. 3,224,861
3. The comparison compound No. 2 is disclosed in U.S. Pat. No. 3,303,014

Example B

Test of Effects on Paddy-field Weeds Under Irrigation Conditions With Water-applied Pre-emergence Treatment Before Transplanting of Rice Seedlings After filling up Wagner pots that were 1/5,000 are in area with sieved soil from a paddy field, further soil containing a large quantity of seeds of barnyard grass and seeds of other common paddy-field weeds was uniformly incorporated in the sieved soil to a depth of 2 cm from the soil surface. Then cut pieces of spikerush(2 × 2 cm) were planted in the soil surface, followed by irrigation to a depth of 4 cm above the soil.

To each of the pots, the active compound was administered dropwise, in the form of a formulation prepared as described in the Example A, at a fixed quantity by means of a pipette. Thirty minutes later, rice seedlings (Kinmaze variety) at the two-leaved stage were planted at the centre of the soil surface. The irrigation water was discharged for 2 days at a rate of 2 cm per day, and thereafter maintained at a depth of about 3 cm.

After 4 weeks, the herbicidal effect on the weeds and the phytotoxicity to the rice plants were evaluated in the manner described in Example A.

The results of the test are shown in Table B.

Table B.

Test of effects on paddy-field weeds under irrigation conditions with
water-applied pre-emergence treatment before transplanting of rice seedlings

| Compound | Amount of active ingredient (g/10 are) | Herbicidal Effect | | | | Phytotoxicity towards Rice plants |
|---|---|---|---|---|---|---|
| | | Barnyard grass | Umbrella-sedge | Spikerushes | Broad-leaved weeds | |
| 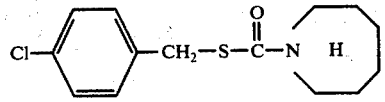 (I) | 300<br>150<br>75 | 5<br>5<br>5 | 5<br>5<br>5 | 4–5<br>4–5<br>4 | 5<br>5<br>5 | 0<br>0<br>0 |
| 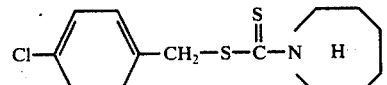 (Comparison No.1) | 1500<br>1000<br>500 | 4<br>3<br>0 | 4<br>4<br>0 | 3<br>0<br>0 | 3<br>0<br>0 | 2<br>1<br>0 |
| 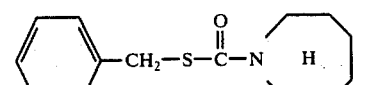 (Comparison No.2) | 600<br>300<br>150 | 5<br>4<br>3 | 4<br>4<br>3 | 3<br>2<br>0 | 4<br>2<br>0 | 5<br>4<br>3 |
|  (Comparison No. 3) | 600<br>300<br>150 | 4<br>2<br>0 | 4<br>2<br>0 | 2<br>0<br>0 | 3<br>1<br>0 | 4<br>2<br>0 |
| 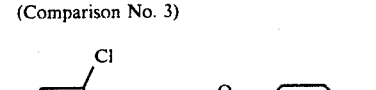 (Comparison No. 4) | 600<br>300<br>150 | 5<br>3<br>1 | 4<br>3<br>0 | 3<br>0<br>0 | 3<br>2<br>0 | 4<br>2<br>1 |

Table B.-continued
Test of effects on paddy-field weeds under irrigation conditions with water-applied pre-emergence treatment before transplanting of rice seedlings

| Compound | Amount of active ingredient (g/10 are) | Herbicidal Effect | | | | Phytotoxicity towards Rice plants |
|---|---|---|---|---|---|---|
| | | Barnyard grass | Umbrella-sedge | Spikerushes | Broad-leaved weeds | |
| 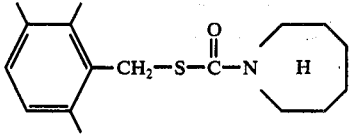 (Comparison No. 5) | 600<br>300<br>150 | 4<br>2<br>1 | 4<br>3<br>1 | 2<br>1<br>0 | 3-4<br>2<br>0 | 3<br>2<br>0 |
| Non-Treatment | — | 0 | 0 | 0 | 0 | 0 |

Note: Broad-leafed weeds: Monochoria, *Rotala indica* and *Lindernia pyxidaria*

EXAMPLE C

Test of Effects on Paddy-field Weeds Under Irrigation Conditions With Water-applied Pre-emergence Treatment After Transplantation of Rice Seedlings After filling up Wagner pots that were 1/5,000 are in area with soil from a paddy field, rice seedlings (Kinmaze variety) at the 2-leaved stage (about 10 cm in height) were transplanted into the pots at a rate of 2 seedlings per pot. Soil containing a large quantity of seeds of barnyard grass and of other common paddy-field weeds was uniformly incorporated into the pots to a depth of 2 cm from the soil surface and cut pieces (2 × 2 cm) of spikerush were planted in the soil. The pots were subsequently irrigated to a depth of 3 cm. The active compound was administered in the form of an emulsion, prepared as described in Example A, at a fixed quantity by means of a pipette shortly after the transplantation of the rice seedlings. After the application, the irrigation water was discharged for 2 days at a rate of 2 - 3 cm per day, and was thereafter maintained at a depth of about 3 cm.

After 4 weeks, the herbicidal effect on the weeds and the phytotoxicity to the rice plants were evaluated in the manner described in Example A.

The results of the test are shown in Table C.

Table C.
Test of effects on paddy-field weeds under irrigation conditions with water-applied pre-emergence treatment after transplantation of rice seedlings

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 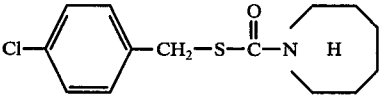 (I) | 300<br>150<br>75 | 5<br>5<br>5 | 5<br>5<br>5 | 5<br>4-5<br>4 | 5<br>5<br>5 | 0<br>0<br>0 |
| 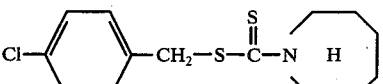 (Comparison No. 1) | 1500<br>1000<br>500 | 4<br>2-3<br>0 | 3-4<br>3<br>0 | 3<br>0<br>0 | 3<br>0<br>0 | 0<br>0<br>0 |
| 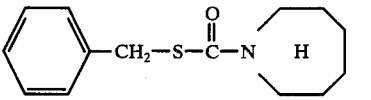 (Comparison No. 2) | 600<br>300<br>150 | 5<br>3-4<br>3 | 4<br>3<br>2 | 3<br>1<br>0 | 4<br>2<br>0 | 4<br>3<br>2 |
| 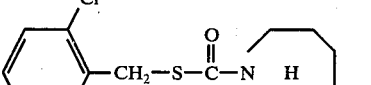 (Comparison No. 3) | 600<br>300<br>150 | 4<br>2<br>0 | 3-4<br>2<br>0 | 3<br>1<br>0 | 3<br>1<br>0 | 3<br>1<br>0 |
|  (Comparison No. 4) | 600<br>300<br>150 | 5<br>4<br>2 | 4<br>3<br>0 | 2-3<br>1<br>0 | 3<br>2<br>1 | 2<br>0<br>0 |

Table C.-continued

Test of effects on paddy-field weeds under irrigation conditions
with water-applied pre-emergence treatment after transplantation of rice seedlings

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 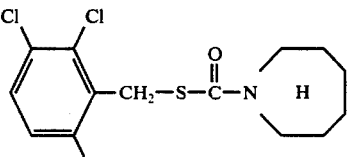 (Comparison No. 5) | 600<br>300<br>150 | 4<br>2<br>1 | 4<br>3<br>0 | 2-3<br>2<br>1 | 4<br>2<br>0 | 2<br>1<br>0 |
| Non-Treatment | — | 0 | 0 | 0 | 0 | 0 |

Notes: Broad-leafed weeds: *Monochoria, Rotala indica* and *Lindernia pyxidaria*

EXAMPLE D

Test of Effects on Paddy-field Weeds Under Irrigation Conditions With Water-Applied Post-emergence Treatment After filling up Wagner pots that were 1/5,000are in area with soil from a paddy field, rice seedlings (Kinmaze variety) at the 2-leaved stage (about 10 cm in height) were transplanted into the pots at a rate of 2 seedlings per pot. Soil containing a large quantity of seeds of barnyard grass and seeds of other common paddy field weeds was uniformly incorporated in the pots to a depth of 2 cm from the soil surface, and then cut pieces of spikerush (2 × 2 cm) were planted in the soil surfaces. Subsequently the pots were kept in moist conditions. When the barnyard seeds had grown to the two-to three-leaved stage (10 days after sowing), the pots were watered to a depth of 6 cm. The active compound was administered in the form of an emulsion, prepared as described in Example A, at a fixed quantity by means of a pipette.

After the application, the irrigation water was discharged for 2 days at a ratio of 2 -3 cm per day and was thereafter maintained at a depth of about 3 cm.

After 4 weeks, the herbicidal effect on the weeds and the phytotoxicity to the rice plants were evaluated in the manner described in Example A.

The results of the test are shown in Table D.

Table D.

Test of effects on paddy-field weeds under irrigation conditions
with water-applied post-emergence treatment

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 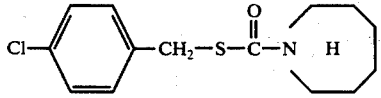 (I) | 400<br>200<br>100 | 5<br>5<br>4-5 | 5<br>5<br>4-5 | 4-5<br>4-5<br>4 | 5<br>5<br>4-5 | 0<br>0<br>0 |
| 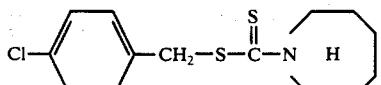 (Comparison No. 1) | 2000<br>1500<br>1000 | 3<br>0<br>0 | 1<br>0<br>0 | 0<br>0<br>0 | 3<br>1<br>0 | 0<br>0<br>0 |
| 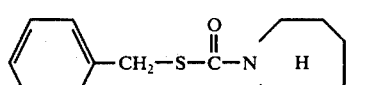 (Comparison No. 2) | 800<br>500<br>200 | 4<br>2<br>0 | 3<br>1<br>0 | 0<br>0<br>0 | 3-4<br>2<br>0 | 4<br>4<br>2 |
| 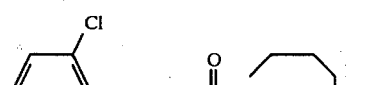 (Comparison No. 3) | 800<br>500<br>200 | 2<br>0<br>0 | 2<br>0<br>0 | 1<br>0<br>0 | 3<br>2<br>0 | 4<br>3<br>0-1 |

Table D.-continued

Test of effects on paddy-field weeds under irrigation conditions with water-applied post-emergence treatment

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 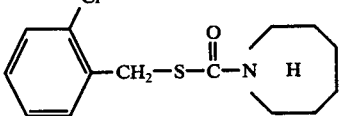 (Comparison No. 4) | 800 500 200 | 3-4 2 1 | 3 2 0 | 0 0 0 | 4 3 2 | 3-4 2 0 |
| 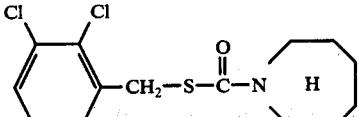 (Comparison No. 5) | 800 500 200 | 3 2 0 | 2 1 0 | 0 0 0 | 3-4 2 1 | 4 2 0 |
| Non-treatment | — | 0 | 0 | 0 | 0 | 0 |

Notes: Broad-leafed weeds: Monochoria, *Rotala indica* and *Lindernia pyxidaria*

EXAMPLE E

Test of Effects on Paddy-field Weeds under Irrigation Conditions with Soil Incorporation Treatment (concrete vessel test)

A concrete vessel with a length of 50 cm, a width of 50 cm and a height of 30 cm was used for the test.

On the bottom of the vessel, a 3 cm layer of gravel, a 2 cm layer of sand and a 3 cm layer of soil from a paddy field were formed in that sequence and they were pressed until compact. These layers were then covered with sieved soil from a paddy field to a height of 10 cm. The vessel was watered to a depth of about 2 cm. The active compound was scattered on the soil in the form of granules, prepared as described in Example (iv), in a fixed quantity and was incorporated into the soil to a depth of 10 cm from the soil surface. To the treated soil, further soil containing a large quantity of seeds of barnyard grass and seeds of other common paddy-field weeds was uniformly incorporated to a depth of 2 cm from the soil surface. Then, 2 rice seedlings (Kinmaze variety) at the 2-leaved stage were planted in each of four different areas of the soil and cut pieces of spike-rush (2 × 2 cm) were planted in the soil surface. Thereafter, the vessel was irrigated to a depth of about 4 cm, while discharging the irrigation water for 2 days at a rate of 2 cm per day. Then, the irrigation water was kept at a depth of about 3 cm.

After 4 weeks, the herbicidal effect on the weeds and the phytotoxicity to the rice plants were evaluated in the manner described in Example A.

The results of the test are shown in Table E.

Table E.

Test of effects on paddy-field weeds under irrigation conditions with soil-incorporation treatment (concrete vessel test)

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 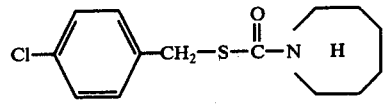 (I) | 600 400 200 | 5 5 4 | 5 5 5 | 5 5 4 | 5 5 5 | 0 0 0 |
| 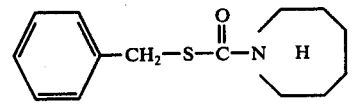 (Comparison No. 2) | 1000 750 500 | 3 3 2 | 4 3 2 | 0 0 0 | 2 0 0 | 4 4 3 |
| 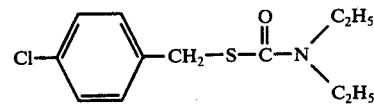 (Comparison No. 6) | 600 400 200 | 5 3 1 | 5 4 3 | 4-5 3 2 | 4 2 0 | 2 0 0 |

Table E.-continued

Test of effects on paddy-field weeds under irrigation conditions with soil-incorporation treatment (concrete vessel test)

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 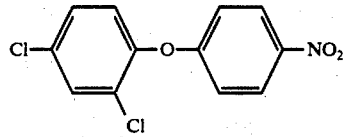 (Comparison No. 7) | 600<br>400<br>200 | 5<br>2<br>0 | 4<br>3<br>0 | 3<br>0<br>0 | 3<br>3<br>0 | 3<br>1<br>0 |
| Non-treatment | — | 0 | 0 | 0 | 0 | 0 |

Notes:
1. Broad-leaved weeds: *Monochoria, Rotala indica* and *Lindernia pyxidaria.*
2. Comparison No. 6, 4-chlorobenzyl-N,N-diethylthiolcarbamate (general name "*benthiocarb*") is commercially available under the trade-name "*Satan*".
3. Comparison No. 7, 2,4-dichlorophenyl 4'-*nitrophenyl ether* (general name "*nitrofen*") is commercially available under the trade-name "*Nippu*".

EXAMPLE F

Test of Effects on Paddy-field Weeds under Irrigation Conditions with Water-applied Preemergence Treatment before Transplantation of Rice Seedlings (concrete vessel test)

A concrete vessel with a length of 50 cm, a width of 50 cm and a height of 30 cm was used for this test.

On the bottom of the vessel, a 3 cm layer of gravel, a 2 cm layer of sand and a 3 cm layer of soil from a paddy field were formed in that sequence and they were pressed compact.

The uppermost soil layer was then covered with sieved soil from a paddy field to a height of 10 cm. Into the so-formed soil layer, further soil, containing a large quantity of seeds of barnyard grass and seeds of other common paddyfield weeds, was uniformly incorporated to a depth of 2 cm from the soil surface, and cut pieces of spikerush (2 × 2 cm) were planted in the soil. Thereafter, the vessel was watered to a depth of about 4 cm, and the active compound was scattered on the soil in the form of granules, as described in Example E, at a fixed quantity. After one hour, 2 rice seedlings (Kinmaze variety) at the 2-leaved stage were planted at each of four different areas of the soil, while discharging the irrigation water for 2 days at a rate of 2 cm per day. Subsequently, the irrigation water was kept at a depth of about 3 cm.

After 4 weeks, the herbicidal effect on the weeds and the phytotoxicity to the rice plants were evaluated in the manner described in Example A.

The results of the test are shown in Table F.

Table F.

Test of effects on paddy-field weeds under irrigation conditions with pre-emergence soil surface treatment before transplantation of rice seedlings (concrete vessel test)

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 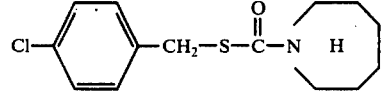 (I) | 300<br>150<br>75 | 5<br>5<br>5 | 5<br>5<br>5 | 4-5<br>4<br>3 | 5<br>5<br>5 | 0<br>0<br>0 |
| 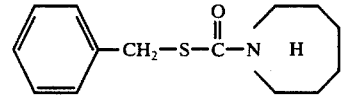 (Comparison No. 2) | 600<br>400<br>200 | 5<br>3<br>2 | 4<br>4<br>3 | 3-4<br>2<br>0 | 3<br>1<br>0 | 5<br>4<br>3 |
| 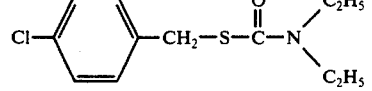 (Comparison No. 6) | 300<br>150<br>75 | 5<br>4<br>2 | 5<br>5<br>3 | 4<br>3<br>2 | 4<br>3<br>1 | 1<br>0<br>0 |
| 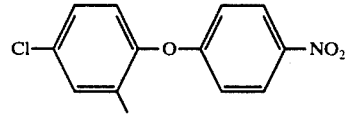 (Comparison No. 7) | 400<br>200<br>100 | 5<br>3-4<br>0 | 5<br>4<br>0 | 3<br>2<br>0 | 5<br>4<br>0 | 4<br>2-3<br>0 |
| Non-treatment | — | 0 | 0 | 0 | 0 | 0 |

Notes: Broad-leafed weeds; Monochoria, *Rotala indica* and *Lindernia pyxidaria*

EXAMPLE G

Test against Paddy-field Weeds under Irrigation Conditions with Water-applied Pre-emergence Treatment after Transplantation of Rice Seedlings (concrete vessel test)

A concrete vessel with a length of 50 cm, a width of 50 cm and a height of 30 cm was used for this test.

On the bottom of the vessel, a 3 cm layer of gravel, a 2 cm layer of sand and a 3 cm layer of soil from a paddy field were formed in that sequence and these layers were pressed until compact.

The uppermost soil layer was then covered with sieved soil from a paddy field to a height of 10 cm. Into the so-formed soil layer, further soil, containing a large quantity of seeds of barnyard grass and seeds of other common paddy-field weeds, was uniformly incorporated to a depth of 2 cm from the soil surface, and cut pieces of spikerush (2 × 2 cm) were planted in the surface layer of soil. Then, two rice seedlings (Kinmaze variety) at the 2-leaved stage were planted at each of four different areas of the soil. Immediately thereafter, the active compound was scattered on the soil in the form of granules, as described in Example E, at a fixed quantity, while discharging the irrigation water for two days at a rate of 2 cm per day. Thereafter, the irrigation water was kept at a depth of 3 cm.

After 4 weeks, the herbicidal effects on the weeds and the phytotoxicity to the rice plants were evaluated in the manner described in Example A.

The results of the test are shown in Table G.

Notes: Broad-leafed weeds: Monochoria, *Rotala indica* and *Lindernia pyxidaria*

EXAMPLE H

Test of Effects on Paddy-field Weeds under Irrigation Conditions with Water-applied Post-emergence Treatment (concrete vessel test)

A concrete vessel with a length of 50 cm, a width of 50 cm and a height of 30 cm was used for this test.

On the bottom of the vessel, a 3 cm layer of gravel, a 2 cm layer of sand, and a 3 cm layer of soil from a paddy field were formed in that sequence. There layers were pressed until compact.

The uppermost soil layer was then covered with sieved soil from a paddy field to a height of 10 cm. Into the so-formed soil layer, further soil, containing a large quantity of seeds of barnyard grass and seeds of other common paddy-field weeds, was uniformly incorporated to a depth of 2 cm from the soil surface, and cut pieces of spikerush (2 × 2 cm) were planted in the soil. Then, two rice seedlings (Kinmaze variety) at the 2-leaved stage were planted at each of four different areas of the soil in each vessel. After ten days, when the barnyard grass had grown to its 2-leaved stage, the active compound was scattered on the soil in the form of granules, as described in Example E, at a fixed quantity. Immediately after the application of the compound, the irrigation water was discharged for two days at a rate of 3 cm per day. Thereafter the irrigation water was kept at a depth of 4 cm.

After 4 weeks, the herbicidal effects on the weeds and the phytotoxicity to the rice plants were evaluated in the manner described in Example A.

The results of the test are shown in Table H.

Table G.

Test of effects on paddy-field weeds under irrigation conditions with water-applied pre-emergence treatment after transplantation of rice seedlings (concrete vessel test)

| Compound | Amount of active ingredient (g/10 are) | Herbicidal Effect | | | | Phytotoxicity towards rice plants |
|---|---|---|---|---|---|---|
| | | Barnyard grass | Umbrella-sedge | Spikerushes | Broad-leaved weeds | |
| 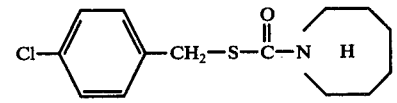 (I) | 300<br>150<br>75 | 5<br>5<br>5 | 5<br>5<br>5 | 5<br>4<br>3 | 5<br>5<br>5 | 0<br>0<br>0 |
| 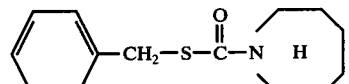 (Comparison No. 2) | 600<br>400<br>200 | 5<br>3–4<br>3 | 4–5<br>4<br>3 | 3–4<br>3<br>2 | 3<br>1<br>0 | 5<br>4<br>3 |
| 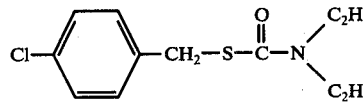 (Comparison No. 6) | 300<br>150<br>75 | 5<br>4<br>3 | 5<br>5<br>4 | 4–5<br>4<br>3 | 4–5<br>3<br>1 | 0<br>0<br>0 |
| 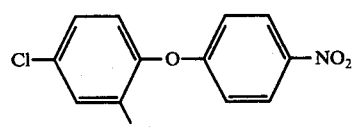 (Comparison No. 7) | 400<br>200<br>100 | 5<br>3–4<br>0 | 5<br>5<br>0 | 4<br>2<br>0 | 5<br>4<br>0 | 4<br>1–2<br>0 |
| Non-treatment | — | 0 | 0 | 0 | 0 | 0 |

Table H

Test of effects on paddy-field weeds under irrigation conditions with water-applied post-emergence treatment (concrete vessel test)

| Compound | Amount of active ingredient (g/10 are) | Herbicidal Effect | | | | Phytotoxicity towards rice plants |
| --- | --- | --- | --- | --- | --- | --- |
| | | Barnyard grass | Umbrella-sedge | Spikerushes | Broad-leaved weeds | |
| 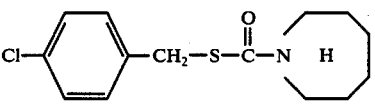 (I) | 400 | 5 | 5 | 4-5 | 5 | 0 |
| | 200 | 4 | 5 | 4 | 4-5 | 0 |
| | 100 | 4 | 4-5 | 3 | 4 | 0 |
| 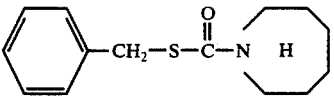 (Comparison No. 2) | 800 | 3-4 | 4 | 2 | 3-4 | 4 |
| | 500 | 3 | 3 | 0 | 0 | 3 |
| | 200 | 0 | 0 | 0 | 0 | 2 |
| 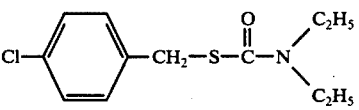 (Comparison No. 6) | 400 | 4 | 5 | 4-5 | 4 | 1 |
| | 200 | 3 | 3 | 3 | 3 | 0 |
| | 100 | 1 | 2 | 3 | 1 | 0 |
| 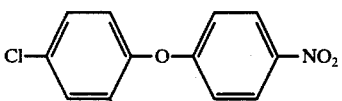 (Comparison No. 7) | 600 | 4 | 4 | 3 | 5 | 5 |
| | 400 | 2 | 3 | 0 | 4 | 4 |
| | 200 | 0 | 0 | 0 | 0 | 0 |
| Non-treatment | — | 0 | 0 | 0 | 0 | 0 |

Note: Broad-leafed weeds: Monochoria, *Rotala indica* and *Lindernia pyxidaria*

As is apparent from the above-stated test results, the herbicidal compositions used in the present invention show not only an excellent compatibility with rice plants but also surprising herbicidal activities against the common paddy-field weeds, barnyard grass, spike-rushes, and broad-leaved weeds.

Furthermore, the said herbicidal compositions are characterized by a far longer application period than the prior-art herbicidal compositions.

As demonstrated by the results of Example A dealing with soil treatment, the present herbicidal compositions show a remarkable selectivity with respect to the root systems of rice plants. Therefore, the reduction of the benefits of the herbicidal effects owing to damage to the crop plants by the chemically treated soil layer, which damage has so far been unavoidable, can be eliminated. Accordingly, the present herbicidal compositions can be applied not only before germination but also in combination with fertilizers, so that considerable labour in cultivation can be saved.

As is clear from Examples B and C, the present herbicidal compositions can be applied either immediately before or after the transplantation of the rice-plant seedlings without the fear of any phytotoxicity. Therefore, one can equip a sprayer with a seedling-transplanting machine, so that extra labour in spraying the chemical can be saved. Moreover, since the present herbicidal compositions can be effectively used for pre-emergence soil-surface treatment, the dosage can be low, whilst retaining the maximum effects.

As is clear from Example D, the present herbicidal compositions exhibit adequate activity even after the germination of aquatic weeds, which fact in turn provides a long period of effective application. This means that farmers can obtain sufficient herbicidal effects from the present herbicidal compositions, even if they miss the customary time for application.

It will be understood that the specification and examples are illustrated but not limitative of the present invention and that other embodiments within the spirit and scope of the invention will suggest themselves to those skilled in the art.

What is claimed is:

1. Method of combating undesired vegetation in paddy field rice, which method comprises applying to the weeds or a weed habitat the compound of the formula

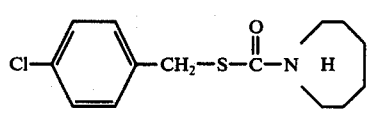

(I)

alone or in admixture with a diluent or carrier.

2. Method as claimed in claim 1, in which said compound is applied in a composition containing 0.001 to 10% of the active compound, by weight.

3. Method as claimed in claim 2, in which said compound is applied in a composition containing 0.005 to 5% of the active compound, by weight.

4. Method as claimed in claim 1, in which the active compound is applied to an area of agriculture in an amount of 0.5 to 20 kg per hectare.

5. Method as claimed in claim 4, in which the active compound is applied in an amount of 1 to 10 kg per hectare.

* * * * *